(12) United States Patent  
Itsuji (10) Patent No.: US 9,261,401 B2  
(45) Date of Patent: Feb. 16, 2016

(54) APPARATUS CONFIGURED TO GENERATE TERAHERTZ WAVE AND APPARATUS CONFIGURED TO DETECT TERAHERTZ WAVE

(71) Applicant: CANON KABUSHIKI KAISHA, Tokyo (JP)

(72) Inventor: Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 60 days.

(21) Appl. No.: 14/300,069

(22) Filed: Jun. 9, 2014

(65) Prior Publication Data  
US 2014/0361177 A1 Dec. 11, 2014

(30) Foreign Application Priority Data  
Jun. 11, 2013 (JP) .................................. 2013-123219

(51) Int. Cl.  
*G01J 1/00* (2006.01)  
*G01J 1/04* (2006.01)  
*G01J 3/42* (2006.01)  
*G01J 3/02* (2006.01)  
*G01N 21/3581* (2014.01)  
*G01N 21/3586* (2014.01)

(52) U.S. Cl.  
CPC ............. *G01J 1/0448* (2013.01); *G01J 3/0208* (2013.01); *G01J 3/42* (2013.01); *G01N 21/3581* (2013.01); *G01N 21/3586* (2013.01)

(58) Field of Classification Search  
CPC .. G01J 1/0448; G01J 3/0208; G01N 21/3581; G01N 21/3586; G01N 21/35; H01S 1/02; G02B 13/14  
See application file for complete search history.

(56) References Cited

U.S. PATENT DOCUMENTS

| | | | | |
|---|---|---|---|---|
| 5,789,750 A * | 8/1998 | Nuss | ......................... | G01J 3/42 250/330 |
| 7,426,171 B2 * | 9/2008 | Shinoda | ................. | B82Y 10/00 369/112.01 |
| 7,884,942 B2 * | 2/2011 | Umetsu | ................. | G01J 3/0208 250/336.1 |
| 7,965,440 B2 * | 6/2011 | Holzwarth | ................ | G01J 1/58 359/326 |
| 8,294,106 B2 * | 10/2012 | Nakajima | ................ | H01Q 9/16 250/353 |
| 2011/0215245 A1 * | 9/2011 | Ouchi | ........................ | G01J 3/42 250/338.4 |
| 2012/0153161 A1 * | 6/2012 | Han | .......................... | G01J 3/42 250/353 |

FOREIGN PATENT DOCUMENTS

JP 2009-124437 A 6/2009  
JP 4762944 B2 8/2011  
WO WO2011/215245 * 9/2011

* cited by examiner

*Primary Examiner* — Yara B Green  
(74) *Attorney, Agent, or Firm* — Canon USA Inc. IP Division (57) ABSTRACT

An apparatus including: an element configured to generate or detect a terahertz wave; a semi-spherical lens configured to guide the terahertz wave outgoing from the element or entering the element; and a holder configured to hold the semi-spherical lens and the element in a state in which a flat surface of the semi-spherical lens and the element are in contact with each other or in a state in which the flat surface of the semi-spherical lens and the element clamp a substance which allows the terahertz wave to pass therethrough and the flat surface of the semi-spherical lens and the element are in contact with the substance, wherein the holder includes: a resiliently deformable portion; and a position adjusting unit configured to adjust a relative position between the semi-spherical lens and the element in a direction parallel to the flat surface of the semi-spherical lens by resiliently deforming the resiliently deformable portion.

11 Claims, 9 Drawing Sheets

B-B' CROSS SECTION

C-C' CROSS SECTION

D-D' CROSS SECTION

E-E' CROSS SECTION

APPARATUS CONFIGURED TO GENERATE TERAHERTZ WAVE AND APPARATUS CONFIGURED TO DETECT TERAHERTZ WAVE

BACKGROUND OF THE INVENTION

1. Field of the Invention

This disclosure relates to an apparatus configured to generate a terahertz wave or an apparatus configured to detect a terahertz wave.

2. Description of the Related Art

A terahertz wave is an electromagnetic wave having a component falling within a given frequency range in a range from 0.03 THz to 30 THz. In such a frequency range, many types of characteristic absorption coming from structure or condition of various substances such as biological molecules as a principal example exist. By using the characteristics described above, an inspection technology configured to perform analysis and identification of substances in a non-destructive manner is developed. In addition, application to a tomography apparatus configured to visualize interiors of substances, in which an imaging technology, a high-speed communication technology, and transmissivity of the terahertz wave are effectively utilized, is expected.

Examples of a method of achieving generation and detection of the terahertz wave include a method of irradiating a light conductive element with a femtosecond laser. The light conductive element is obtained by forming a semiconductor film provided with an antenna electrode at a minute space on a substrate.

In order to improve efficiency of isolating the terahertz wave outgoing from the light conductive element, or efficiency of importing the terahertz wave into the terahertz wave incoming into the light conductive element, a semi-spherical lens having the same degree of refractive index as the substrate having the semiconductor film formed thereon is used. The semi-spherical lens is used with a flat surface portion thereof tightly in contact with a surface of the substrate having the antenna electrode formed thereon.

In order to improve efficiency of isolating and the efficiency of importing of the terahertz wave, alignment of an optical axis of the semi-spherical lens (an axis of rotational symmetry) and the antenna electrode of the light conductive element is important.

As a method performing the alignment, Japanese Patent No. 4762944 discloses a method of fixing the positions of the semi-spherical lens and the light conductive element by fitting the semi-spherical lens and components such as the light conductive element in a plurality of depressed portions formed on a holder configured to hold the semi-spherical lens and the light conductive element. In this case, accuracy of alignment is determined by the processing accuracy or the size of the depressed portions.

In order to confirm whether the alignment between the semi-spherical lens and the element is achieved with high degree of accuracy, detection of the terahertz wave by actually using an apparatus configured to generate or detect the terahertz wave and observation of an intensity or an amplitude of the detected terahertz wave are needed. When the alignment is insufficient, the alignment needs to be performed again. In the case of the configuration as Japanese Patent No. 4762944, the apparatus needs to be disassembled once and assembled again. Therefore, alignment cannot be performed while observing the intensity or the like of the terahertz wave. Therefore, the operation of the alignment may become complicated.

SUMMARY OF THE INVENTION

According to an aspect of this disclosure, there is provided an apparatus including: an element configured to generate or detect a terahertz wave; a semi-spherical lens configured to guide the terahertz wave outgoing from the element or entering the element; and a holder configured to hold the semi-spherical lens and the element in a state in which a flat surface of the semi-spherical lens and the element are in contact with each other or in a state in which the flat surface of the semi-spherical lens and the element clamp a substance which allows the terahertz wave to pass therethrough and the flat surface of the semi-spherical lens and the element are in contact with the substance, wherein the holder includes: a resiliently deformable portion; and a position adjusting unit configured to adjust a relative position between the semi-spherical lens and the element in a direction parallel to the flat surface of the semi-spherical lens by resiliently deforming the resiliently deformable portion.

Further aspects of the present invention will become apparent from the following description of exemplary embodiments with reference to the attached drawings.

DESCRIPTION OF THE EMBODIMENTS

A mode in which an idea of this disclosure can be implemented will be described with reference to the drawings.

Figure 1A:
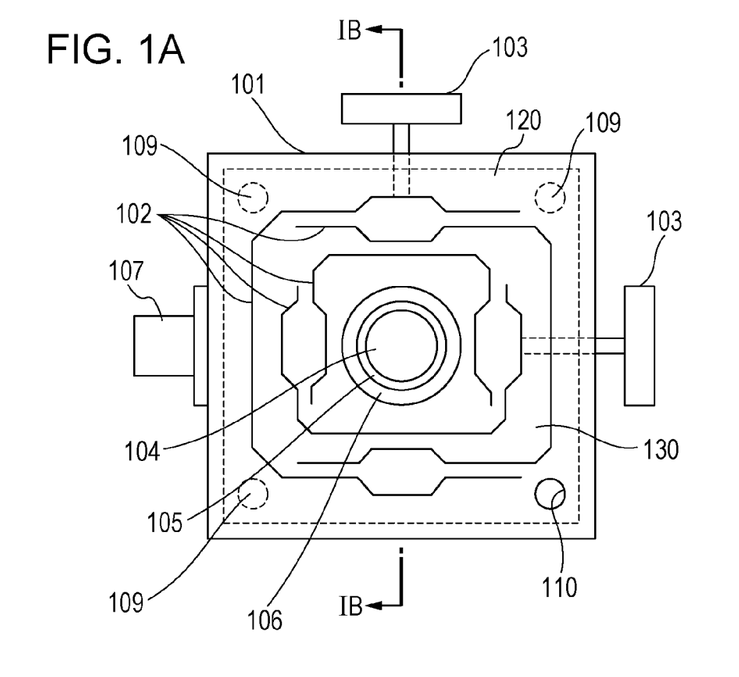
FIG. 1A is a front view of an apparatus of an embodiment.
Figure 1B:
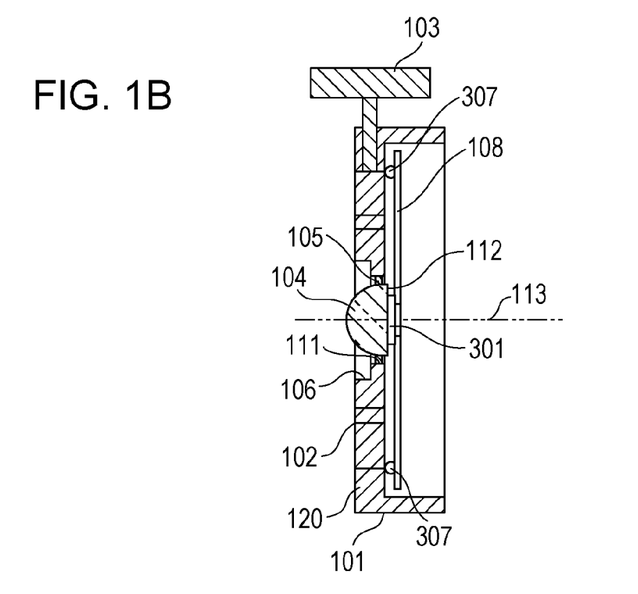
FIG. 1B is a cross-sectional view of an apparatus of an embodiment.

FIG. 1A and FIG. 1B are drawings configured to explain a configuration of an apparatus configured to generate or detect a terahertz wave, which is an apparatus of the embodiment.

FIG. 1A is a front view of the apparatus, and FIG. 1B is a cross-sectional view of the apparatus taken along a line IB-IB.

A configuration of the apparatus will be described. The apparatus of the embodiment includes a holder 101, a semi-spherical lens 104, an element 301, and an element holding substrate 108 for arranging the element 301.

The holder 101 is mainly a part including a flat panel 120 configured to hold the semi-spherical lens 104 and the element holding substrate 108. The material of the holder 101 may either be a metal or a resin, but preferably is formed of a conductive substance for reducing noise. In FIG. 1B, a back surface of the holder 101 is opened. However, the back surface may be closed depending on the applications.

A flat panel 120 of the holder 101 includes a depressed portion 106, and is formed with a through hole 111 at a center of the depressed portion 106. The through hole 111 is a portion where the semi-spherical lens 104 is arranged. In this embodiment, a lens holding portion 105 provided in the through hole 111 holds the semi-spherical lens 104. More specifically, a screw groove is provided on an inner surface of the through hole 111, and the lens holding portion 105 is a resin ring having a screw corresponding to the screw groove.

The inner diameter of the lens holding portion 105 is smaller than the diameter of the semi-spherical lens 104. The lens holding portion 105 is arranged on a curved surface side of the semi-spherical lens 104, and the lens holding portion 105 is rotated and pushed into the through hole 111, whereby the semi-spherical lens 104 is sandwiched between the lens holding portion 105 and the element 301 arranged on the element holding substrate 108. The element 301 is arranged on a flat surface side of the semi-spherical lens 104. Consequently, the holder 101 holds the semi-spherical lens 104. The position where the lens holding portion 105 and the semi-spherical lens 104 are in contact with each other will be described later.

The material of the lens holding portion 105 is not limited to the resin, and may be a metallic material. In order to prevent the semi-spherical lens 104 from braking, an interfering member such as an O-ring may be inserted to a position where the semi-spherical lens 104 and the lens holding portion 105 are in contact with each other. The depressed portion 106 is provided so as to prevent the interference between the terahertz wave and the holder 101. In the case where the interference between the terahertz wave and the holder 101 is not recognized even without the depressed portion 106, the depressed portion 106 may be omitted.

The semi-spherical lens 104 includes a flat surface 112, an at least part of the flat surface 112 is in contact with the substrate of the element 301 configured to generate or detect the terahertz wave. Since the terahertz wave passes through the interior of the semi-spherical lens 104, the semi-spherical lens 104 is preferably formed of a material which allows the terahertz wave to pass easily therethrough. Specifically, a high-resistance silicon and an olefin-based resin material are exemplified.

In order to prevent unnecessary reflection from occurring on the flat surface 112 of the semi-spherical lens 104 between the semi-spherical lens 104 and the element 301, the difference in refractive index between the material of the semi-spherical lens 104 an the material of the element 301 is preferably small.

The holder 101 further includes substrate holding portions 109 configured to hold the element holding substrate 108. The element 301 is fixed to the holder 101 by holding the element holding substrate 108 which holds the element 301 by the holder 101.

The element holding substrate 108 is a substrate configured to hold the element 301, and includes engaging portions 307 corresponding to the substrate holding portions 109 provided with the holder 101. The positioning of the holder 101 and the element holding substrate 108 is performed by the substrate holding portions 109 and the engaging portions 307. Specific positioning structures will be described later.

The holder 101 includes a connector 107 configured to relay the connection with respect to an external apparatus. The connector 107 has an inherent impedance, and has the same impedance as the apparatus to be connected to the exterior and the cable. Commercially available connectors such as a BNC connector and an SMA connector may be applied as the connector 107.

Figure 2A:
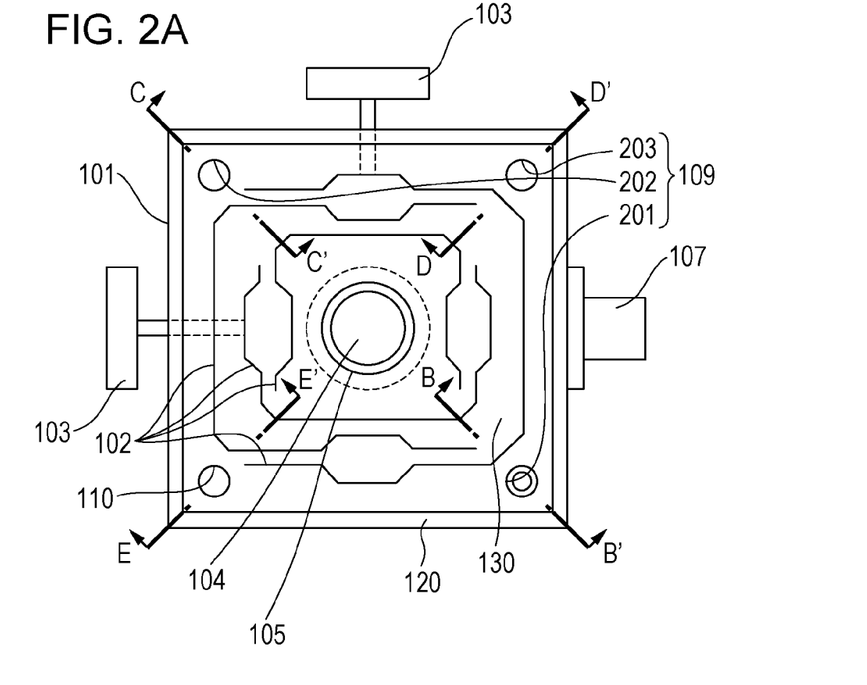
FIG. 2A is a back view of a holder of the embodiment.
Figure 2B:
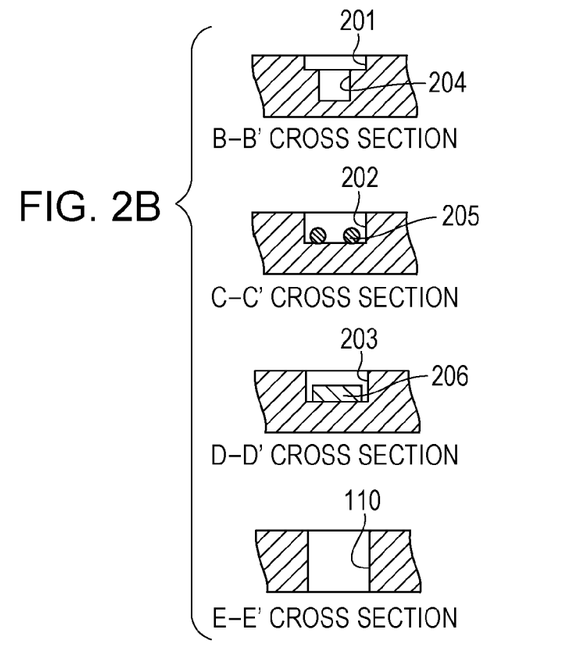
FIG. 2B illustrates cross-sectional views of positioning structures of the holder of the invention.

FIG. 2A and FIG. 2B are drawings for explaining an example of configuration of the substrate holding portions 109 provided on the holder 101. FIG. 2A is a back view of the holder 101, and FIG. 2B illustrates cross-sectional views of the positioning structures. Each of the substrate holding portions 109 at least includes a first positioning hole 201, a second positioning hole 202, and a third positioning hole 203. In this specification, a surface of the holder 101 on which the element 301 and the element holding substrate 108 are arranged is defined as the back surface of the holder 101.

The first positioning hole 201 includes a positioning reference hole 204. The first positioning hole 201 is provided with the positioning reference hole 204 on a bottom of a circular hole. The center of the circular hole and the center of the positioning reference hole 204 are preferably the same.

A positioning ball 304 which constitutes the engaging portion 307, which will be described later, is fitted to the positioning reference hole 204, and constitutes a reference point when positioning the element holding substrate 108 with respect to the holder 101. Therefore, the diameter of the positioning reference hole 204 is smaller than the diameter of the positioning ball 304. In a state in which the positioning ball 304 is fitted to the positioning reference hole 204, the element holding substrate 108 is allowed to rotate about the positioning reference hole 204 as a reference point in a plane parallel to the flat surface 112 of the semi-spherical lens 104.

The second positioning hole 202 includes a positioning groove 205. The second positioning hole 202 is a circular hole, and the positioning groove 205 is constituted by two rods fixed to a bottom surface of the second positioning hole 202. These rods are arranged in parallel to each other. More specifically, the rods are arranged so that the positioning groove 205 extends substantially perpendicularly to a line connecting the first positioning hole 201 and the second positioning hole 202. The groove width of the positioning groove 205 is smaller than the diameter of the positioning balls 304, which constitute the engaging portions 307.

When positioning the element holding substrate 108 with respect to the holder 101, the positioning ball 304 is fitted to the positioning groove 205, and is used together with the first positioning hole 201. Accordingly, the element holding substrate 108 is positioned with limited flexibility in rotation with respect to a direction substantially parallel to the flat surface 112 of the semi-spherical lens 104 with respect to the holder 101. When a distance exists between the element holding substrate 108 and the holder 101, the element holding substrate 108 is allowed to rotate about a straight line connecting the first positioning hole 201 and the second positioning hole 202. Although the positioning groove 205 is constituted by the rods, the positioning groove 205 may be formed by machining a groove on the bottom surface of the second positioning hole 202.

The third positioning hole 203 includes a positioning surface 206. The third positioning hole 203 is a circular hole, and the positioning surface 206 is a flat panel member fixed to the bottom surface of the third positioning hole 203.

When positioning the element holding substrate 108 with respect to the holder 101, the positioning balls 304 which constitute the engaging portions 307 are brought into abutment with the positioning surface 206. The positioning surface 206 adjusts the position of abutment by the thickness of the flat panel member of the positioning surface 206. Accordingly, parallelism of the element holding substrate 108 with respect to the holder 101 is determined. Specifically, the positioning of the element holding substrate 108 with respect to the holder 101 is performed by limiting the flexibility in the direction of rotation about the straight line connecting the first positioning hole 201 and the second positioning hole 202.

Although the flat panel member is used for the formation of the positioning surface 206, the flat panel member may be omitted by adjusting the depth of the third positioning hole 203 and machining the bottom surface into a flat surface.

The positioning method described above is based on a kinematic positioning method which limits the flexibility in all directions of rotation for achieving the positioning of the member. Therefore, the known kinematic positioning method may be applied to the positioning of the element holding substrate 108 with respect to the holder 101. For example, in the description given above, the positioning is achieved with lines and surfaces by using the positioning reference hole 204, the positioning groove 205, and the positioning surface 206. However, all may have the same structure as the positioning groove 205. The positioning surface 206 may have the same structure as the positioning groove 205.

Figure 3A:
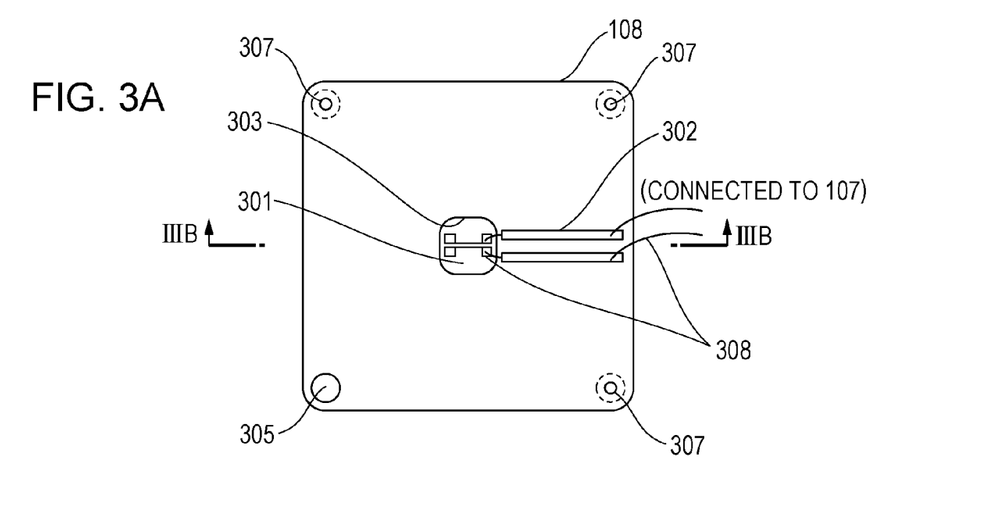
FIG. 3A is a top view of an element holding substrate of the embodiment.
Figure 3B:
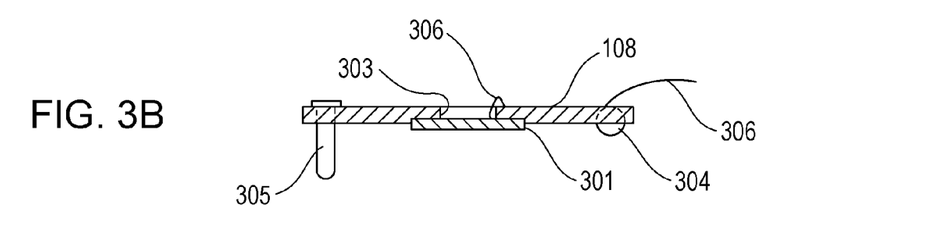
FIG. 3B is a cross-sectional view of the element holding substrate of the embodiment.
Figure 3C:
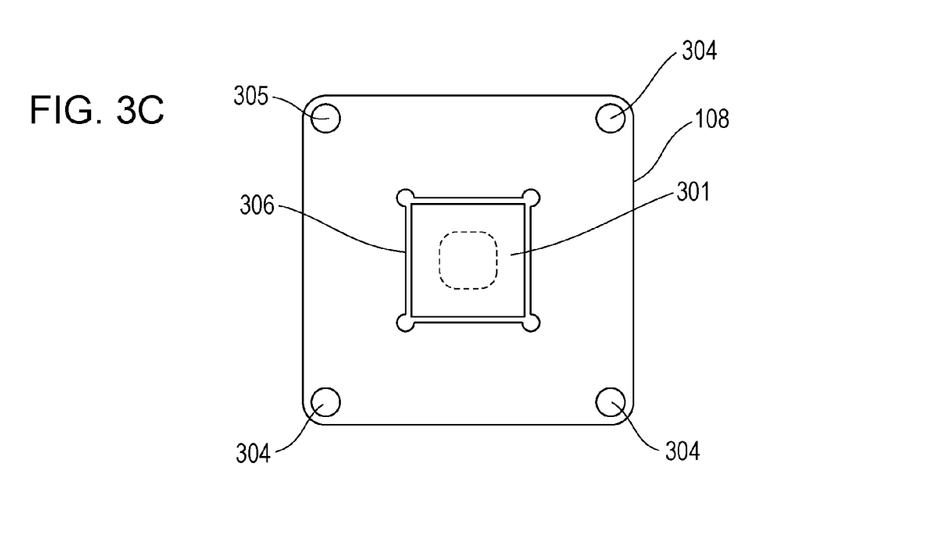
FIG. 3C is a back view of the element holding substrate of the embodiment.

An example of configuration of the element holding substrate 108 will be described with reference to FIG. 3A, FIG. 3B, and FIG. 3C. FIG. 3A illustrates a surface of the element holding substrate 108, FIG. 3B is a cross-sectional view of the element holding substrate 108 taken along a line IIIB-IIIB, and FIG. 3C is a back view of the element holding substrate 108. The element holding substrate 108 is a substrate for arranging the element 301 thereon. The material of the element holding substrate may be any one of a metal, a resin, and ceramic. In this specifically, the surface of the element holding substrate is a surface having an exposed portion 303 on which a portion of the element 301 which generates or detects the terahertz wave is to be arranged, and a surface opposite thereto is defined as a back surface. The semi-spherical lens 104 is arranged on a back surface side. The portion of the element 301 which generates or detects the terahertz wave corresponds to a position suitable for being irradiated with light for generating the terahertz wave with high degree of efficiency, or a position suitable for being irradiated with light and the terahertz wave for detecting the terahertz wave with high degree of sensitivity.

In this embodiment, the element 301 is a light conductive element having an antenna electrode and a power feed electrode patterned on a semiconductor substrate. As the semiconductor substrate, for example, a gallium arsenide (GaAs) substrate or indium gallium arsenide (InGaAs) may be applied. A low-temperature grown gallium arsenide (LT-GaAs) film or indium gallium arsenide (LT-InGaAs) film is formed on the semiconductor substrate. On the semiconductor film, the antenna electrode and the power feed electrode are patterned.

Part of the semiconductor substrate may be replaced by a member causing a lesser loss of the terahertz wave (for example, a high-resistance silicone). The material of the semiconductor substrate is not limited thereto, and the known material that can generate and detect the terahertz wave may be applied. The shape of the antenna electrode is designed as needed according to the wavelength and the spectrum shape of the terahertz wave to be used. Typically, the shape of the antenna electrode is designed to have a size from several to several tens of micrometer.

Although the example of the light conductive element has been exemplified as a mode of the element 301, the element 301 is not limited thereto, and this disclosure may be applied to a known generating unit or detecting unit such as a resonance tunnel diode, or a shot-key barrier diode. More specifically, any modes may be applied as long as the semi-spherical lens 104 is used as a space coupler for the generating unit and the detecting unit to be used, and the alignment between the semi-spherical lens 104 and the element 301 is necessary.

The light conductive element generates and detects the terahertz wave by an ultrashort pulsed-femtosecond laser.

In FIG. 3A, the element holding substrate 108 includes the exposed portion 303, and part of the element 301 is arranged so as to be exposed from the exposed portion 303. At this time, the portion of the element 301 that generates or detects the terahertz wave (which corresponds to the antenna electrode in the case of the light conductive element) is arranged to a position near the center of the exposed portion 303. More specifically, the element holding substrate 108 includes an element installing portion 306 for installing the element 301 (FIG. 3B, FIG. 3C). The element installing portion 306 includes a depressed portion extending along a contour of the element 301, and the element 301 is fixed by being fitted to the depressed portion. An adhesive agent may be used as a fixing device.

As illustrated in FIG. 3C, with the provision of relief portions at four corners of the element installing portion 306, the element 301 can be fitted to the depressed portion of the element installing portion 306 even though four corners of the element 301 have a right angle. Therefore, the positioning accuracy at the time of fixation of the element 301 to the element holding substrate 108 may be enhanced. In the case where the adhesive agent is used for the fixation of the element 301, excessive adhesive agent generating when the element 301 is pressed against the element holding substrate 108 is accumulated in the relief portions, and hence a probability of adhesion of the adhesive agent to the element 301 is reduced.

The element holding substrate 108 includes lines 302 for relaying the connector 107 and the power feed electrode of the element 301. As described above, the connector 107 is connected to the external apparatus, and hence the lines 302 may be referred to as the lines 302 for relaying the element 301 and the external apparatus in other words.

The lines 302 are connected to the connector 107 and the power feed electrodes of the element 301 via metallic thin wires 308. Preferably, the lines 302 are transmission lines having an impedance matching that of the external apparatus. FIG. 3A, FIG. 3B, and FIG. 3C illustrate an example in which the transmission lines are composed of striplines. The striplines are adjusted in distance so as to match the impedance of the external apparatus. The transmission lines are not limited to the striplines, and known forms of the transmission lines such as microstriplines or coplanar strip lines may be applied.

The element holding substrate 108 includes the engaging portions 307. The engaging portions 307 include three of the positioning balls 304 arranged so as to correspond to the substrate holding portions 109.

The substrate holding portions 109 or the engaging portions 307 may be formed of a magnetic material to fix the substrate holding portions 109 and the engaging portions 307 with a magnetic force. For example, the positioning balls 304 which constitute the engaging portions 307 are composed of magnetic balls, and the positioning reference hole 204, the positioning groove 205, and the positioning surface 206 which constitute the substrate holding portions 109 are formed of a metal which attracts a magnet.

Alternatively, the positioning reference hole 204, the positioning groove 205 and the positioning surface 206 are formed of magnet, and the positioning balls 304 are formed of a metal which attracts the magnet. Forming the positioning reference hole 204, the positioning groove 205, the positioning surface 206, and the positioning balls 304 of a magnet is also conceivable.

In this configuration, the holder 101 and the element holding substrate 108 are fixed in position by a magnetic force simultaneously with the positioning, the components (screw or the like) required for the fixation may be reduced, and workability at the time of replacement of the element is improved.

The first positioning hole 201, the second positioning hole 202, and the third positioning hole 203 which constitute the substrate holding portions 109 are preferably arranged on a circumference of a concentric circle centered at the through hole 111. In addition, the engaging portions 307 corresponding thereto are preferably arranged on a circumference of a concentric circle centered at the through hole 111. The respective positioning structure preferably includes a certain degree of distance from the through hole 111. In this arrangement, since the distance between the respective positioning holes to the terahertz wave passing through the through hole 111 are set to be long and the same, the positioning accuracy is improved.

A configuration in which one of the holder 101 and the element holding substrate 108 includes a guide hole for fixing the element holding substrate 108 to the holder 101, and the other one of those includes a guide pin. In this embodiment, an example in which the holder 101 includes a guide hole 110 penetrating through the holder 101 is illustrated in FIG. 1A. Then, the element holding substrate 108 in FIG. 3A includes a guide pin 305 to be inserted into the guide hole 110.

When positioning and fixing the holder 101 and the element holding substrate 108, a distal end of the guide pin 305 of the element holding substrate 108 is aligned with the guide hole 110 of the holder 101. Subsequently, the element holding substrate 108 can be positioned and fixed in a form of placing the guide pin 305 along the guide hole 110.

In this configuration, when attaching the element holding substrate 108 to the holder 101, the holder 101 and the element holding substrate 108 can be arranged along the guide pin 305 and the guide hole 110. Therefore, when replacing the element, the element 301 mounted on the element holding substrate 108, a risk of breakage that the element 301 mounted on the element holding substrate 108 is broken by being brought into contact with respective parts of the holder 101 inadvertently is reduced.

The holder 101 may have a mechanism that clamps the guide pin 305. For example, a configuration in which an outer screw structure is formed at a distal end of the guide pin 305 and the element holding substrate 108 is fixed with a nut provided on the guide hole 110 is also applicable.

A configuration in which a screw hole for clamping is provided through the guide hole 110 in a direction intersecting the guide hole 110 from the outside of the holder 101, the guide pin 305 is inserted therethrough, and a screw is tightened thereon for fixation is also applicable.

In this manner, with the provision of the separate mechanism for clamping the guide pin, a holding force of the element holding substrate 108 positioned on the holder 101 is improved.

Referring back to FIG. 1A, a resiliently deformable portion 130 provided on the holder 101 will be described in detail. The resiliently deformable portion 130 in this specification is formed by the provision of opening portions 102 in the flat panel 120 which constitute the holder 101, and is a portion being resiliently deformed when a force is applied from the outside. Therefore, the opening portions 102 are positioned adjacent to the resiliently deformable portion 130. The opening portions 102 which forms the resiliently deformable portion 130 are arranged in a pattern combining a plurality of U-shaped thin openings (grooves). The resiliently deformable portion 130 is a portion configured to be resiliently deformed by being applied with an external force and, consequently, changing the position of the through hole 111.

The resiliently deformable portion 130 is formed around the through hole 111. The relative position between the element 301 and the semi-spherical lens 104 in the direction parallel to the flat surface 112 can be changed by moving the through hole 111 in the direction parallel to the flat surface 112 of the semi-spherical lens 104.

As illustrated in FIG. 1A and FIG. 2A, the resiliently deformable portion 130 is formed into the U-shaped patterns formed around the through hole 111 of the holder 101. More specifically, the resiliently deformable portion 130 of this embodiment is configured by arranging the two openings (grooves) of a U-shaped pattern in a nested structure so as to oppose each other as illustrated in FIG. 1A.

The resiliently deformable portion 130 is resiliently deformed by being applied with a force from the outside, and moves the through hole 111 located at the center thereof. Here, by employing the nested structure for the resiliently deformable portion 130, deformations of the through hole 111 in the direction different from the direction of application of the force are balanced out. Therefore, the through hole 111 is moved in the same direction as the direction of the force applied to the resiliently deformable portion 130.

The resiliently deformable portion 130 is preferably provided inside a circle having a radius corresponding to the distance from the center of the through hole 111 and the substrate holding portions 109. The distance from the center of the through hole 111 and the substrate holding portion 109 is defined as a distance from the center of the through hole 111 to a center of any one of the first to third positioning reference holes 201, 202, and 203 which constitute the substrate holding portion.

The opening portions 102 which form the resiliently deformable portion 130 of this embodiment are arranged in such a manner that two nested structures are arranged so that one of the two nested structures is rotated by 90 degrees about the through hole 111. Therefore, the through hole 111 may be moved in the direction parallel to the flat surface 112.

When the through hole 111 moves by the resilient deformation of the resiliently deformable portion 130, the semi-spherical lens 104 arranged in the through hole 111 also moves. In contrast, since the position of the element 301 is positioned and fixed to the holder 101, the relative position between the semi-spherical lens 104 and the element 301 can be changed.

Figure 4:
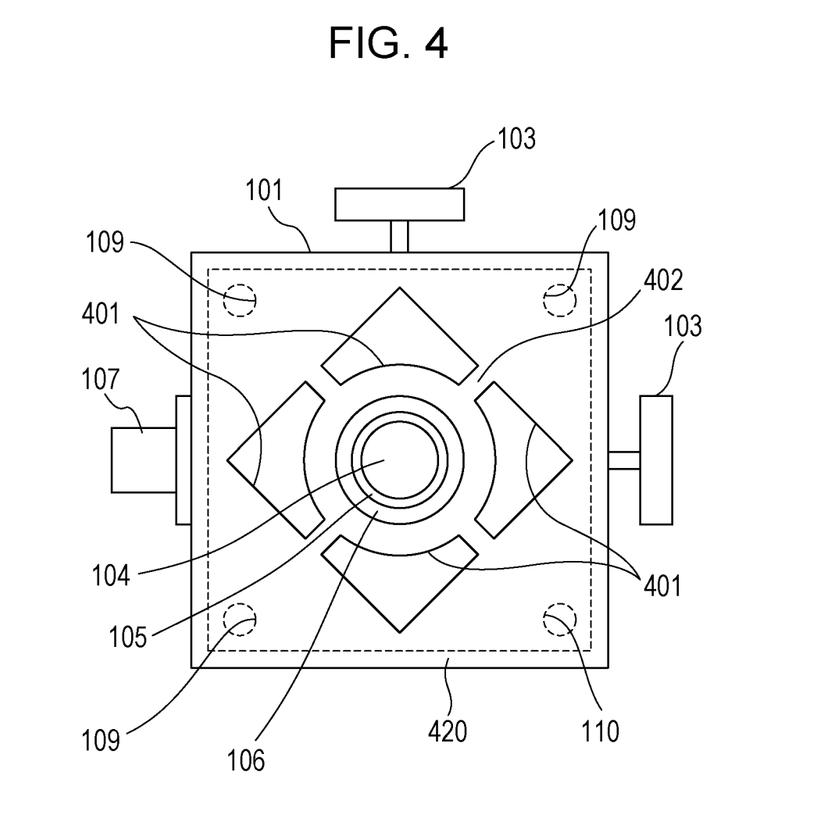
FIG. 4 is a drawing for explaining an example of patterns of an opening portion.

The pattern of the opening portions 102 which constitutes the resiliently deformable portion 130 is not limited to the pattern described above, and any structure may be employed as long as the part of the flat panel 120 is resiliently deformed by the force applied from the outside and move the through hole 111. For example, a pattern illustrated in FIG. 4 and a pattern used in a piezoelectric table may be applied. A resiliently deformable portion 402 illustrated in FIG. 4 is formed by forming four openings about the through hole 111 to form an opening portion 401 in a flat plate 420 provided in the holder. As a matter of course, other configurations may be applied as long as the position of the through hole 111 is changed by the resilient deformation.

In order to apply a force to the resiliently deformable portion 130, the holder 101 includes an actuator 103 as a position adjusting unit which resiliently deforms the resiliently deformable portion 130. The actuator 103 of this embodiment is of a type that performs an adjustment by manually rotating a screw. However, adjustment maybe performed remotely by combining a motor. The device for applying the force is not limited to a type which feeds by using the screw, and a method of moving the position of the member (which corresponds to a screw in the case of the type that feeds by using the screw) for applying the power by using a piezoelectric motor or an ultrasonic motor.

A configuration in which the element 301 is moved by providing the resiliently deformable portion on the element holding substrate 108 is also applicable. However, since the size of the element 301 is smaller than that of the semi-spherical lens 104, a configuration in which the relative position of the both is adjusted by using the semi-spherical lens 104 is preferable.

In this configuration, the through hole 111 and the semi-spherical lens 104 arranged in the through hole 111 are moved in the holder 101 by the resilient deformation of the resiliently deformable portion 130. Consequently, the adjustment of the relative position between the semi-spherical lens 104 and the element 301 in the direction parallel to the flat surface 112 of the semi-spherical lens 104 is achieved. Since the resilient deformation of the member which constitutes the holder 101 is utilized, a retaining force for retaining the adjusted position is strong, and hence long-last stability is maintained. Since part of the holder 101 is mechanically machined to form the resiliently deformable portion 130, a stage for moving the semi-spherical lens 104 is not necessary to provide separately, so that a reduction in size of the apparatus is realized.

The positioning utilizing the resilient deformation uses a balance between a force applied to the resiliently deformable portion 130 and a repulsive force generated by the resilient deformation. Therefore, for example, in comparison with the mode in which the alignment is performed with the positioning accuracy of micrometer, a higher positioning accuracy is achieved, so that the efficiency of isolating and efficiency of importing the terahertz wave are improved. The relative position between the element 301 in the direction parallel to the flat surface 112 of the semi-spherical lens 104 and the semi-spherical lens 104 can be changed, so that the accuracy of the adjustment is enhanced in comparison with the mode in which the position of the semi-spherical lens 104 is fixed with respect to the element 301. Therefore, the efficiency of isolating and the efficiency of importing the terahertz wave are improved.

Figure 5:
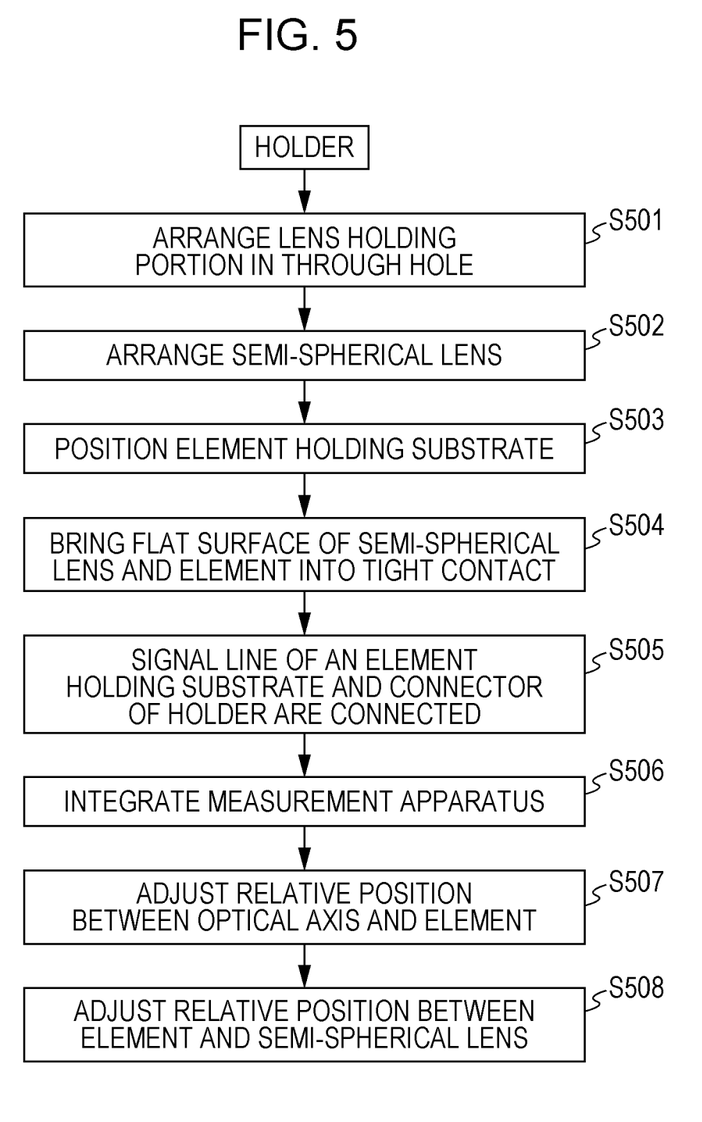
FIG. 5 is a flowchart relating to a positioning of the apparatus of the embodiment.

The method of positioning the element 301 and the semi-spherical lens 104 with respect to the holder 101 will be described with reference to FIG. 5. FIG. 5 is a flowchart relating to the positioning of the holder, the element, and the semi-spherical lens in the apparatus of this embodiment.

An initial positioning of the element 301 and the semi-spherical lens 104 with respect to the holder 101 will be performed in the following manner. The holder 101 is provided with the actuator 103 as a position adjusting unit. The element 301 is arranged on the element holding substrate 108.

First of all, in Step S501, the lens holding portion 105 is inserted into the through hole 111 provided in the holder 101 from the depressed portion 106 and is fixed to the through hole 111. The inner wall of the through hole 111 and the outside of the lens holding portion 105 are each formed with a screw groove structure, and the lens holding portion 105 is fixed to the through hole 111 by the screw groove structure.

In the lens holding portion 105, a curved surface portion of the semi-spherical lens 104 is arranged from the depressed portion 106 side (S502). The element holding substrate 108 to which the element 301 is fixed is arranged in proximity to the semi-spherical lens 104 along the guide hole 110 from the flat surface side of the semi-spherical lens 104 by utilizing the guide pin 305 provided on the element holding substrate 108 and the guide hole 110 provided in the holder 101.

By placing the element holding substrate 108 on the holder 101 and bringing the substrate holding portions 109 and the engaging portion 307 into engagement, the alignment is achieved (S503). Specifically, by the three positioning balls 304, which constitute the engaging portions 307, coming into contact respectively with the positioning reference hole 204, the positioning groove 205, and the positioning surface 206 which constitute the substrate holding portions 109, the positioning of the element 301 with respect to the holder 101 is achieved. In this embodiment, the both components are fixed by a magnetic force.

Subsequently, by rotating the lens holding portion 105 with respect to the through hole 111, the semi-spherical lens 104 is pressed against the element 301 held by the element holding substrate 108. In this manner, in a state in which the semi-spherical lens 104 and the element 301 are held by the holder 101 in tight contact with each other (S504).

In Step S505, the signal line (metallic thin wire) 308 of the element holding substrate 108 and the connector 107 of the holder 101 are electrically connected. In this manner, since the positioning of the semi-spherical lens 104 and the element 301 with respect to the holder can be executed easily by the substrate holding portions 109 and the engaging portions 307 of the holder 101 and the element holding substrate 108, the workability is improved.

Subsequently, by the resilient deformation of the resiliently deformable portion 130 provided on the holder 101, the adjustment of the relative position between the semi-spherical lens 104 and the element 301 in the direction parallel to the flat surface 112 of the semi-spherical lens 104 can be performed. This operation is performed by assembling the apparatus of this embodiment into a measurement apparatus configured to measure the terahertz wave (S506), and observing an output of the terahertz wave.

Specifically, when assembling the apparatus of the embodiment into the measurement apparatus, the apparatus is arranged so that an optical axis 113 and the element 301 are orthogonal to each other and also the optical axis 113 passes through the portion of the element 301 generating or detecting the terahertz wave (S507). At this time, the semi-spherical lens 104 moves so as to follow the movement of the element 301. The optical axis 113 in this specification represents a line which indicates the center of the propagating terahertz wave as a result of the optical adjustment. In this specification, the terahertz wave is also referred to as the optical axis.

After the position of assembly of the apparatus has determined by referring the output of the terahertz wave, the position of the semi-spherical lens 104 is adjusted with respect to the axis orthogonal to the optical axis 113 by the resiliently deformable portion 130 and the actuator 103 (S508).

In this manner, since the positions of the semi-spherical lens 104 and the element 301 can be adjusted while observing the output of the terahertz wave and referring to the result of the observation, the efficiency of isolating and the efficiency of importing of the terahertz wave can be improved. Here, the output of a terahertz wave pulse can be observed from the peak value and the shape of an obtained temporal waveform, or the shape of the frequency spectrum.

FIG. 6A, FIG. 6B, FIG. 7A, and FIG. 7B are drawings illustrating a contact position between the holder 101 and the semi-spherical lens 104. In this embodiment, since the lens holding portion 105 is used for holding the semi-spherical lens 104 on the holder 101, these drawings are explanatory drawings illustrating the contact position between the lens holding portion 105 and the semi-spherical lens 104 in other words.

The portion of the element 301 held by the apparatus of this embodiment generating and detecting the terahertz wave is provided on a surface opposing the surface in contact with the flat surface 112 of the semi-spherical lens 104. In this specification, this surface is referred to as a reference surface. When generating the terahertz wave, the femtosecond laser is converted into the terahertz wave on the reference surface, and passes through the substrate and the semi-spherical lens 104 to be taken to the outside. When detecting the terahertz wave, the terahertz wave is converged to a position where the reference surface and the optical axis intersects.

Figure 6A:
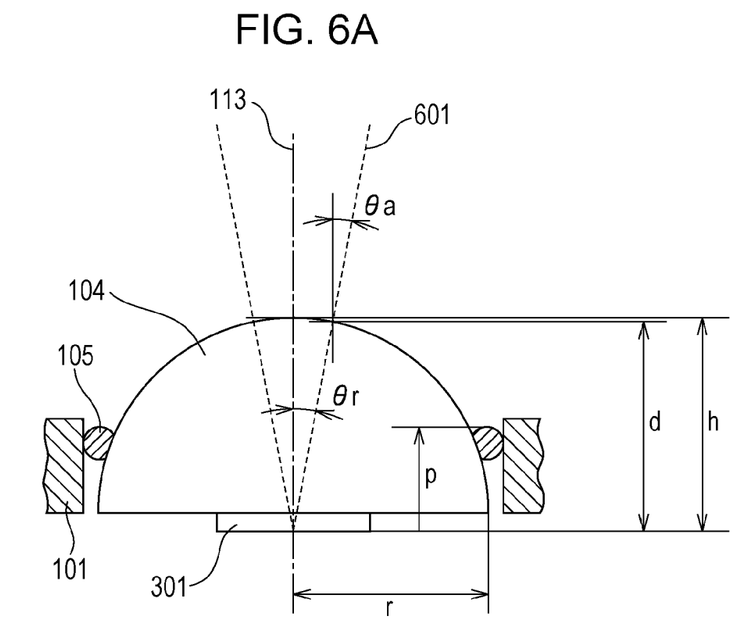
FIG. 6A is a drawing for explaining a contact position of a holder in the case where a hemispherical lens is used as the semi-spherical lens.
Figure 7A:
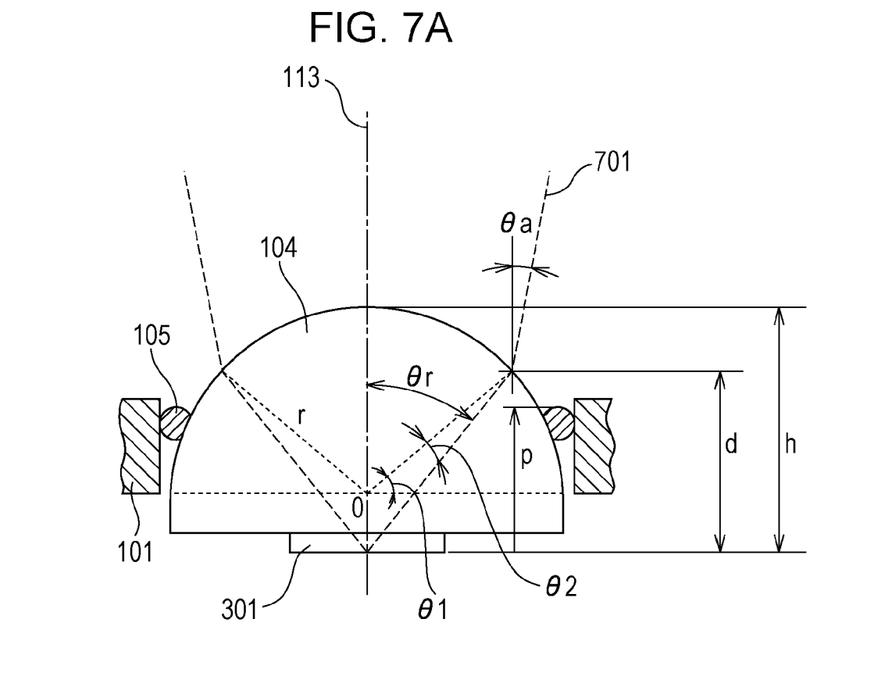
FIG. 7A is a drawing for explaining a contact position of the holder in the case where a collimate lens is used as the semi-spherical lens.

In FIG. 6A and FIG. 7A, a distance d is a shortest distance from the reference surface to a position where the terahertz wave 601 or 701 intersects the curved surface portion of the semi-spherical lens 104. The terahertz wave 601 illustrated in FIG. 6A and a terahertz wave 701 illustrated in FIG. 7A indicate an outline of the range where the terahertz wave propagates.

Figure 6B:
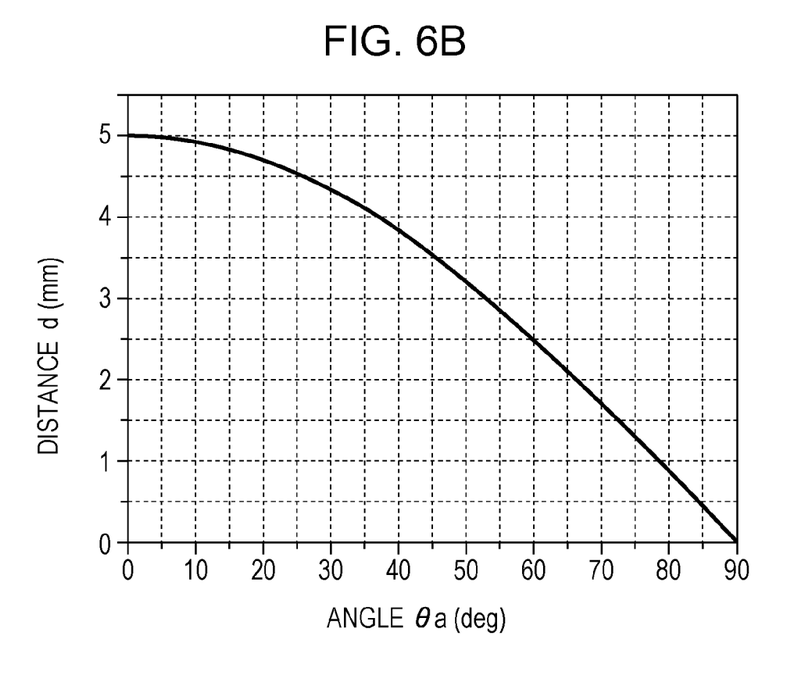
FIG. 6B is a graph for explaining a relationship between an angle θa and a distance d in the case where the hemispherical lens is used as the semi-spherical lens.

Referring now to FIG. 6A and FIG. 6B, a case where a hemispherical lens is used as the semi-spherical lens 104 will be described.

In FIG. 6A, the distance d depends on the shape of the terahertz wave 601, and the terahertz wave 601 can be estimated from a pupil diameter and a focal length of the terahertz wave to be used.

An angle $\theta a$ is an angle formed between a line parallel to the optical axis 113 and an outline of the terahertz wave 601 at a position where the terahertz wave intersects with a curved surface portion of the semi-spherical lens 104. An angle $\theta r$ is an angle of the terahertz wave propagating in the interiors of the semi-spherical lens 104 and the element 301 with respect to the optical axis 113. Here, it is assumed that the semi-spherical lens 104 and the element 301 has the same refractive index.

The shortest distance from the reference surface to an apex of the curved surface portion of the semi-spherical lens 104 is defined as h. In this specification, the shortest distance h is also referred to as a lens height h. A contact position p is a position where the lens holding portion 105 comes into contact with the semi-spherical lens 104. The radius of the semi-spherical lens 104 is r. The semi-spherical lens 104 in FIG. 6A is a semi-spherical lens 104. Therefore, the angle $\theta a$ and the angle $\theta r$ are the same angle. The lens height h has the same value as the radius r.

FIG. 6B is a graph showing a change of the distance d with respect to the angle $\theta a$ in the case where a hemispherical lens is used as the semi-spherical lens 104.

In order to improve the efficiency of isolating and the efficiency of importing of the terahertz wave, at least avoidance of interference with the terahertz wave at the contact position p between the lens holding portion 105 and the semi-spherical lens 104 is needed. Therefore, the shortest distance from the reference surface to the contact position p is preferably smaller than the distance d. The shape of the holder 101 preferably does not intersect the terahertz wave 601.

Subsequently, a case where a collimate lens is used as the semi-spherical lens 104 will be described with reference to FIG. 7A and FIG. 7B.

FIG. 7A illustrates an example in which the collimate lens is used as the semi-spherical lens 104. A description of a portion common to FIG. 6A is omitted. The height h of the collimate lens can be obtained by the following expression. The refractive index of the semi-spherical lens 104 is defined as n.

$$h = r(n+1)/n \quad (1)$$

Here, when a silicon (n=3.3) is used as a material of the semi-spherical lens 104, and the radius r of the semi-spherical lens 104 is defined to be 5 mm, the lens height h becomes approximately 6.5 mm.

In FIG. 7A, a point O is a center position of a ball when the ball having a radius r is assumed. An angle formed between a line connecting a position where the terahertz wave intersects with the curved surface portion of the semi-spherical lens 104 and the point O and a surface perpendicular to the optical axis 113 is defined as an angle $\theta 1$. A line connecting the position where the terahertz wave intersects with the curved surface portion of the semi-spherical lens 104 and the position on the reference surface where the terahertz wave converges is illustrated in FIG. 7A. An angle formed between this line and a line connecting a position where the terahertz wave intersects with the curved surface portion of the semi-spherical lens 104 and the point O is defined as an angle $\theta 2$. At this time, the relationship between the angle $\theta a$ and the distance d can be expressed by the following expressions.

$$\tan(\theta 1 + \theta 2) = \frac{r\sin(\theta 1) + h - r}{r\cos(\theta 1)} \quad (2)$$

$$\sin(\theta 2) = \frac{\cos(\theta a + \theta 1)}{n} \quad (3)$$

$$d = r\sin(\theta 1) + h - r \quad (4)$$

Figure 7B:
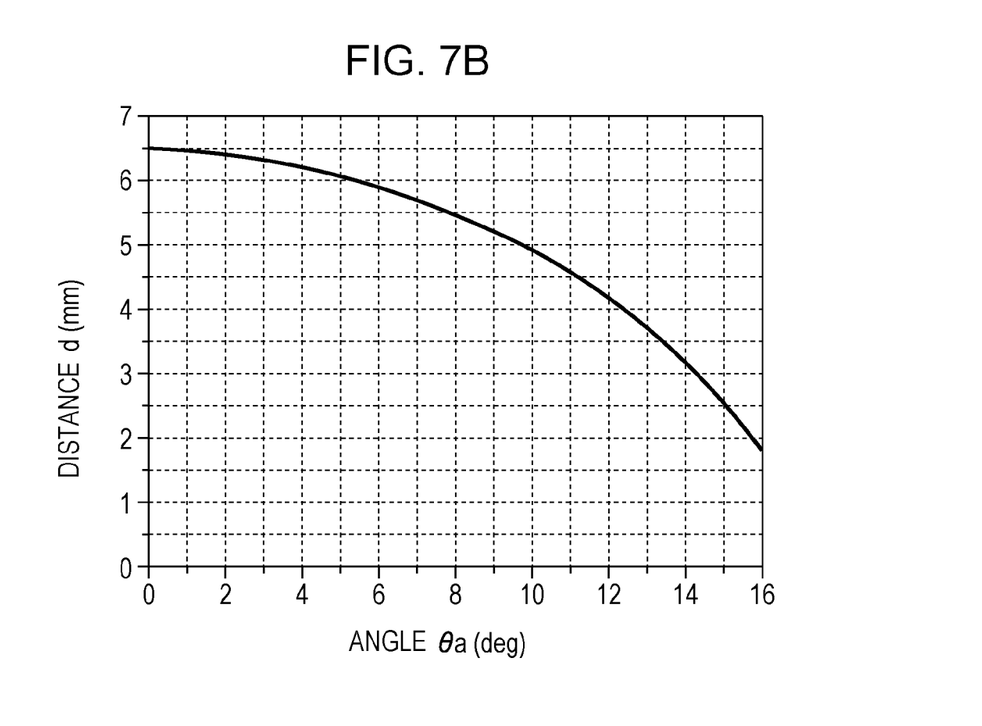
FIG. 7B is a graph for explaining a relationship between an angle θa and a distance d in the case where the collimate lens is used as the semi-spherical lens.

FIG. 7B is a graph showing a change of the distance d with respect to the angle $\theta a$ in the case where a collimator lens in FIG. 7A is used as the semi-spherical lens 104. The distance d depends on the shape of the terahertz wave 701, and the shape of the terahertz wave 701 can be estimated from a pupil diameter and a focal length of the terahertz wave to be used. The angle $\theta r$ of the terahertz wave can be expressed by the following expression.

$$\theta r = 90 - \theta 1 - \theta 2 \quad (5)$$

As described above, in order to improve the efficiency of isolating and the efficiency of importing of the terahertz wave, at least avoidance of interference between the terahertz wave and the apparatus at the contact position p between the lens holding portion 105 and the semi-spherical lens 104 is needed. Therefore, the shortest distance from the reference surface to the contact position p is preferably smaller than the distance d. The shape of the holder 101 preferably does not intersect the terahertz wave 701.

In this manner, by adjusting the contact position between the holder 101 and the semi-spherical lens 104 while considering the shape of the beam of the terahertz wave, mechanical interference between the terahertz wave and the holder is avoided. Therefore, the efficiency of isolating and the efficiency of importing the terahertz wave are improved.

In the description given thus far, the substring holding portion 109 includes the first to the third positioning holes and the engaging portions 307 include three positioning reference holes. This disclosure is not limited to the configuration as described above, and the configuration of the substrate holding portions 109 and the configuration of the engaging portions 307 may be vice versa.

Figure 8:
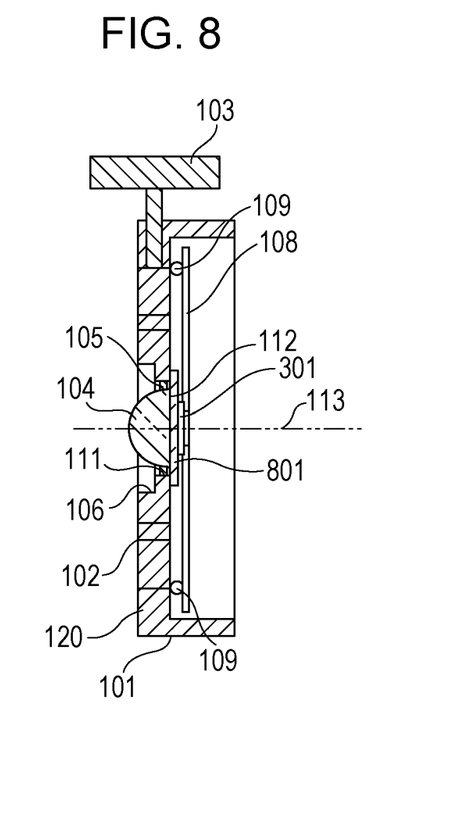
FIG. 8 is a drawing for explaining an example of configuration of the apparatus when an adjusting plate is used.

In the description given thus far, the mode in which the flat surface 112 of the semi-spherical lens 104 and the element 301 fixed to the element holding substrate 108 are in contact with each other has been described. However, as illustrated in FIG. 8, a substance which allows the terahertz wave to pass therethrough such as an adjusting plate 801 may be arranged between the semi-spherical lens 104 and the element 301. The adjusting plate 801 is preferably formed of the same material as the semi-spherical lens 104.

The antenna electrode provided on the element 301 is arranged on a surface opposing the surface which comes into contact with the flat surface 112 of the semi-spherical lens 104. The terahertz wave is preferably converted onto the antenna electrode. Therefore, when the terahertz wave cannot be converted well onto the antenna electrode only with the semi-spherical lens 104, the converging position of the terahertz wave can be adjusted by using the adjusting plate 801.

In this configuration, the focal position of the terahertz wave in the interior of the semi-spherical lens 104 can be adjusted by the adjusting plate 801. Therefore, the flexibility in adjustment is increased, and the efficiency of isolating and the efficiency of importing the terahertz wave are improved.

Matching liquid or the like may be provided between the semi-spherical lens 104 and the element 301 as a substance which allows the terahertz wave to pass therethrough. The substance that allows the terahertz wave to pass therethrough is preferably selected from those having a small difference in refractive index from the semi-spherical lens 104 or the substrate of the element 301. Since the matching liquid serves as lubricant when adjusting the relative position between the semi-spherical lens 104 and the element 301, the probability that damages the components is reduced. In this manner, according to the apparatus of the embodiment as described thus far, the relative position between the semi-spherical lens and the element can be adjusted while observing the terahertz wave.

Figure 9:
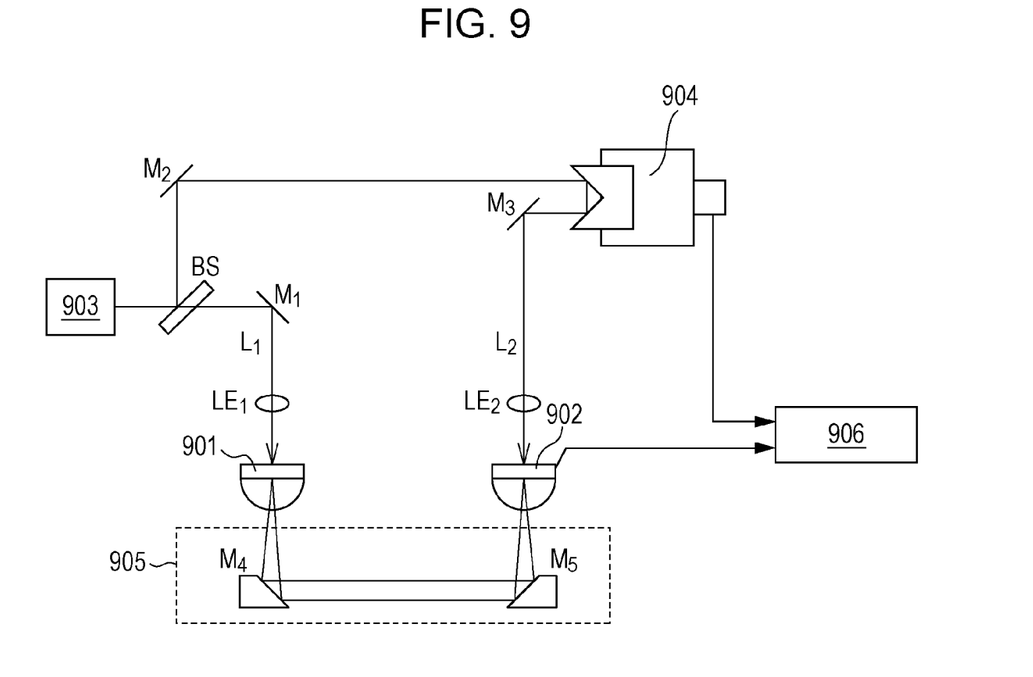
FIG. 9 is a drawing for explaining an example of configuration of an information acquiring apparatus by using the apparatus of the embodiment.

An example of the information acquiring apparatus in which the apparatus of this embodiment is integrated will be described with reference to FIG. 9. FIG. 9 is a drawing illustrating an example of configuration of the information acquiring apparatus in which the apparatus of this embodiment is integrated. The information acquiring apparatus of this embodiment acquires a temporal waveform of the terahertz wave by using a principle of Time Domains Spectroscopy (THz-TDS) for measuring the terahertz wave in a time area. Then, information relating to a sample is acquired by using the acquired temporal waveform.

In the embodiment, a generating unit 901 and a detecting unit 902 are apparatus to which this disclosure is applied, and are a generating unit and a detecting unit for the terahertz wave. Specifically, the generating unit 901 and the detecting unit 902 each include the semi-spherical lens 104 and the element 301 held by the holder 101. A light conductive element is used as the element 301. The configuration of the generating unit is the same as that of the detecting unit. In order to simplify the description, the generating unit is expressed as a generating unit 901, and the detecting unit is expressed as a detecting unit 902.

The information acquiring apparatus of this disclosure includes a shaping unit 905 for converging the terahertz wave pulse outgoing from the generating unit 901 onto the detecting unit 902. In this embodiment, the shaping unit 905 includes two parabolic mirrors of $M_4$ and $M_5$. The configuration of the shaping unit 905 changes in accordance with the mode of usage of the apparatus.

In this embodiment, the apparatus to which this disclosure is applied is used in the generating unit 901 and the detecting unit 902. However, the apparatus to which the invention is applied may be of the mode of being applied to one of the generating unit 901 and the detecting unit 902.

A light source 903 is a part that outputs an exciting light for generating and detecting the terahertz wave pulse. In many cases, the light source 903 outputs a femtosecond laser beam. The femtosecond laser beam output from the light source 903 has a pulse width of several tens of femtosecond.

The exciting light output from the light source 903 is split to $L_1$ which may be referred to as a pump light (hereinafter, referred to as pump light) and $L_2$ (hereinafter, it may be referred to as a probe light).

The pump light $L_1$ enters the element 301 of the generating unit 901 via a mirror $M_1$ and a converging lens $LE_1$. The pump light $L_1$ is used for generating the terahertz wave pulse at the generating unit 901.

A probe light $L_2$ passes through a mirror $M_2$, a delayed optical unit 904, a mirror $M_3$, and a Probe light $L_2$ and enters the element 301 of the detecting unit 902. The probe light $L_2$ is used as sample light for detecting a temporal wavelength of the terahertz wave pulse by the detecting unit 902.

The wavelength of the exciting light output form the light source 903 is changed by a drive wavelength of the generating unit 901 or the detecting unit 902. A wavelength conversion element configured to change the wavelength of the exciting light may be interposed at a midsection of a propagation route of the pump light $L_1$ or the probe light $L_2$. Various characteristics such as the wavelength, the pulse width, and the laser repetition frequency of the exciting light output from the light source 903 are selected as needed according to the required specification of the information acquiring apparatus.

The delayed optical unit 904 is a part configured to adjust the difference in optical path length between the pump light $L_1$, which is exciting light, and the probe light $L_2$. In this embodiment, the temporal waveform of the terahertz wave pulse are acquired by using the principle of a Terahertz Wave Time Domain Spectroscopy. In other words, the information acquiring apparatus performs a sampling measurement on the terahertz wave pulse with the probe light $L_2$ by plotting the output of the terahertz wave as a result of detection by the detecting unit 902 while changing the difference in optical path length of the pump light $L_1$ and the probe light $L_2$ by a predetermined amount.

The method of adjusting the optical path length of the exciting light by the delayed optical unit 904 includes a method of directly adjusting the optical path length of the exciting light, and a method of adjusting an effective optical path length of the exciting light. The method of directly adjusting the optical path length includes a method of using an aliasing optical system configured to fold the exciting light and a method of using a movable unit that moves the folding optical system. A rotating system may be applied as the movable unit. In this case, the folding optical system moves along the direction of rotation in which the movable unit rotates.

A mode in which the pump light $L_1$ and the probe light L2 are output respectively by using two laser sources as the light source 903, and repetition frequencies of the respective laser sources are changed. When the repetition frequencies of the laser sources are different, a time difference between the pump light $L_1$ and the probe light $L_2$ is modulated, so that the difference in optical path length between the pump light $L_1$ and the probe light $L_2$ is converted from a change of the time difference.

The method of adjusting the effecting optical path length includes a method of changing a time constant of the optical path length of the exciting light propagation. In this manner, the delayed optical unit 904 only needs to have a configuration in which the difference in optical path length of the pump light $L_1$ and the probe light $L_2$ can be adjusted. In this embodiment, an example in which the folding optical system and the movable unit are used as the delayed optical unit 904 has been described.

A waveform acquiring unit 906 is a portion which references the difference in optical path lengths of the pump light L1 and the probe light $L_2$ adjusted by the output of the detecting unit 902 and the delayed optical unit 904 and builds the temporal waveform of the terahertz wave pulse. With the configuration of the apparatus as described above, the apparatus acquires the temporal waveform of the terahertz wave.

An information acquiring unit, which is not illustrated, acquires information on the sample by using the temporal waveform acquired by the waveform acquiring unit 906. The information on the sample includes the thickness of the layer in the sample, shapes of the substances existing in the sample, or physical properties of the sample.

When integrating the apparatus in which this disclosure is applied, the output of the terahertz wave acquired by the waveform acquiring unit 906 is observed, and references the results of the observation, thereby performing the optical adjustment. Specifically, the positions of the semi-spherical lens 104 and the element 301 with respect to the optical axis 113 of the terahertz wave are adjusted with reference to the output of the terahertz wave, which is one of the results of observation. More specifically, the position of the element 301 is adjusted by adjusting the position of the holder 101 with respect to the axis orthogonal to the optical axis 113. Then, the relative position of the semi-spherical lens 104 with respect to the optical axis 113 and the element 301 in the direction parallel to the flat surface 112 of the semi-spherical lens 104 is adjusted by the resiliently deformable portion 130 and the actuator 103.

In this manner, since the positions of the semi-spherical lens 104 and the element 301 can be adjusted while observing the terahertz wave by referring to the output of the terahertz wave, result of the observation, the efficiency of isolating and the efficiency of importing of the terahertz wave can be improved.

With the apparatus to which this disclosure is applied, the positions of the element 301 and the semi-spherical lens 104 can be adjusted even when the optical axis of the femtosecond laser beam varies in association with the elapse of time. Therefore, a temporal change is also accommodated.

The "semi-spherical lens" in this specification corresponds to a lens having a flat surface and a curved surface, and includes an ultrahemispherical lens and a collimate lens which handles the parallel beam. The curved surface includes not only a spherical surface as in the embodiment, but also non-spherical surface (parabolic surface, cylindrical surface, conical surface, etc.). The semi-spherical lens may have flat side walls.

The information acquiring apparatus according to this disclosure is capable of measuring part of biological bodies (the skin, or the surfaces of internal organs) of animals or human in vivo. Therefore, the term "sample" in this specification is defined as including not only a substance such as the biological bodies, but also part of the biological bodies.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-123219 filed Jun. 11, 2013, which is hereby incorporated by reference herein in its entirety.

What is claimed is:

1. An apparatus comprising:
an element configured to generate or detect a terahertz wave;
a semi-spherical lens configured to guide the terahertz wave outgoing from the element or entering the element; and
a holder configured to hold the semi-spherical lens and the element in a state in which a flat surface of the semi-spherical lens and the element are in contact with each other or in a state in which the flat surface of the semi-spherical lens and the element clamp a substance which allows the terahertz wave to pass therethrough and the flat surface of the semi-spherical lens and the element are in contact with the substance, wherein
the holder includes:
a resiliently deformable portion; and
a position adjusting unit configured to adjust a relative position between the semi-spherical lens and the element in a direction parallel to the flat surface of the semi-spherical lens by resiliently deforming the resiliently deformable portion.

2. The apparatus according to claim 1, wherein the holder includes a flat panel, and
the flat panel includes the resiliently deformable portion and an opening portion provided at a position adjacent to the resiliently deformable portion.

3. The apparatus according to claim 2, wherein the flat panel includes a through hole in which the semi-spherical lens is arranged, and
the holder includes a substrate holding portion configured to hold an element holding substrate that holds the element on the flat panel.

4. The apparatus according to claim 3, wherein the resiliently deformable portion is provided within a circle having a radius corresponding to a distance from a center of the through hole to the substrate holding portion.

5. The apparatus according to claim 3, wherein the holder includes a lens holding portion configured to fix the semi-spherical lens and the flat panel, and
defining a surface of the element where the terahertz wave of the element is generated or detected as a reference surface, a shortest distance from the reference surface to a position where the semi-spherical lens and the lens holding portion come into contact with each other is smaller than a shortest distance from the reference surface to a position where a curved surface portion of the semi-spherical lens and the terahertz wave intersects.

6. The apparatus according to claim 3, wherein the opening portion includes two nested structures each including two U-shaped narrow openings oppose each other are arranged in such a manner that one of two nested structures is rotated by 90 degrees about the through hole.

7. The apparatus according to claim 3, wherein the element holding substrate includes an engaging portion, and the element holding substrate and the flat panel are fixed by an engagement between the engaging portion and the substrate holding portion.

8. The apparatus according to claim 7, wherein at least one of the substrate holding portion and the engaging portion is formed of a magnetic material, and the substrate holding portion and the engaging portion are fixed by a magnetic force.

9. The apparatus according to claim 1, wherein the semi-spherical lens moves in a direction parallel to a flat surface of the semi-spherical lens by a resilient deformation of the resiliently deformable portion.

10. An apparatus comprising:
   an element configured to generate or detect a terahertz wave;
   a semi-spherical lens configured to guide the terahertz wave outgoing from the element or entering the element; and
   a holder configured to hold the semi-spherical lens and the element in a state in which a flat surface of the semi-spherical lens and the element are in contact with each other or in a state in which the flat surface of the semi-spherical lens and the element clamp a substance which allows the terahertz wave to pass therethrough and the flat surface of the semi-spherical lens and the element are in contact with the substance, wherein
   the holder includes a flat panel, and
   the flat panel includes:
      a substrate holding portion configured to hold an element holding substrate that holds the element on the flat panel;
      a through hole in which the semi-spherical lens is arranged;
      a resiliently deformable portion provided within a circle having a radius corresponding to a distance from a center of the through hole to the substrate holding portion;
      an opening portion provided at a position adjacent to the resiliently deformable portion; and
      a position adjusting unit configured to apply a force to the resiliently deformable portion.

11. An information acquiring apparatus configured to acquire information on a sample, comprising:
   a generating unit configured to generate a terahertz wave, and
   a detecting unit configured to detect the terahertz wave from a sample, wherein
   at least one of the generating unit and the detecting unit is the apparatus according to claim 1.

* * * * *